United States Patent [19]

Maier

[11] 4,434,108
[45] Feb. 28, 1984

[54] HERBICIDALLY ACTIVE 2-NITRO-5-(2'-CHLORO-4'-TRIFLUOROME-THYLPHENOXY)PHENYLPHOSPHINIC ACID DERIVATIVES

[75] Inventor: Ludwig Maier, Arlesheim, Switzerland

[73] Assignee: Ciba-Geigy Corporation, Ardsley, N.Y.

[21] Appl. No.: 280,388

[22] Filed: Jul. 6, 1981

[30] Foreign Application Priority Data

Jul. 9, 1980 [CH] Switzerland ............ 5251/80

[51] Int. Cl.³ .............................................. C07F 9/46
[52] U.S. Cl. ...................................... 260/951; 71/86; 71/87; 260/502.5 D; 260/543 P; 260/940
[58] Field of Search ............ 260/951, 502.5 D, 543 P

[56] References Cited

U.S. PATENT DOCUMENTS 4,322,375 3/1982 Maier et al. ................... 260/940

FOREIGN PATENT DOCUMENTS 7471 2/1980 European Pat. Off. .
14684 8/1980 European Pat. Off. .
2619841 11/1977 Fed. Rep. of Germany .

OTHER PUBLICATIONS

Cadagan et al., "The Reaction of Triethyl Phosphite . . . ", *Chem. Comm. 1966*, 491–492.
Sieper, "Uber eine Bildungsueise . . . Nitrophenyl--Phosphonsävre ester", *Tetrah. Letters No. 21*, 1987–1989 (1967).
Cadogan et al., "The Reactivity of Organophosphorous Compounds, Part XXV . . . ", *J. Chem. Soc. 1969*, 1314–1318.
*Kasolapoff & Maier, Organophosphorus Compounds?*, 226–227.

*Primary Examiner*—Anton H. Sutto
*Attorney, Agent, or Firm*—Frederick H. Rabin

[57] ABSTRACT

The invention relates to novel herbicidally active and plant-growth regulating 2-substituted 5-phenoxy-phenylphosphinic acid derivatives of the formula

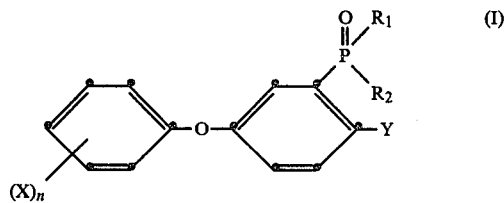

wherein $R_1$ is an unsubstituted or substituted alkyl or aryl radical, $R_2$ is a hydroxyl group, lower alkoxy, alkylthio, alkylamino, dialkylamino or chlorine, X is halogen or is selected from the group consisting of $-CF_3$, $-NO_2$ or $-CN$, n is 0 to 3, and Y is selected from the group consisting of $-NO_2$, $-NH_2$, $-OH$, $-CN$, or is halogen. Preferred compounds are 2-nitro-5-(2'-chloro-4'-trifluoromethylphenoxy)phenylalkylphosphinic acids and lower alkyl esters thereof. The invention also relates to the production of the novel phosphinic acid derivatives, starting from a 3,4-dinitrodiphenyl ether and reaction with a O,O-dialkylalkyl- or -arylphosphonite as first step. The invention further relates to herbicidal and plant growth regulating compositions which contain one of these novel compounds as active component, and also to the use of these compounds and compositions for controlling weeds (also selectively), for inhibiting plant growth and desiccating parts of plants above the ground, as well as for totally destroying existing plant growth.

4 Claims, No Drawings

HERBICIDALLY ACTIVE 2-NITRO-5-(2'-CHLORO-4'-TRIFLUOROMETHYL-PHENOXY)PHENYLPHOSPHINIC ACID DERIVATIVES

The present invention relates to novel plant growth influencing, especially herbicidally active, 2-substituted 5-phenoxy-phenylphosphinic acid derivatives, to the production thereof, to plant growth influencing compositions, especially herbicidal compositions, which contain these novel phosphinic acid derivatives, and to a method of selectively or totally controlling weeds and of regulating plant growth, which comprises the use of these novel compounds and of compositions containing them.

Chlorinated and unchlorinated 2-nitrophenylphosphonic acids and the sodium salts and ethyl esters thereof, have been proposed in German Offenlegungsschrift No. 2 619 841 as active ingredients of compositions for regulating plant growth. Some of the compounds disclosed in this Offenlegungsschrift were already known from earlier publications, such as "Chemical Communications" 1966, 491; J. Chem. Soc. (C) 1969, 1314; and Tetrahedron Letters 1967 (21), 1987–89. The free 2-nitrophenylphosphonic acid is also known to have bactericidal action.

From the series of the phenoxyphenylphosphonic acids, 3-substituted 4-phenoxyphenylphosphonic acids which can be further substituted in the para-position of the phenoxy moiety have been described in "Organic Phosphorus Compounds", ed. G. M. Kopolapoff and L. Maier, John Wiley & Sons Inc., New York, 1976, Vol. 7, pp. 226–227; but no mention of their activity is made.

Herbicidally active 2-substituted 5-phenoxyphenylphosphonic acids and derivatives thereof form the subject matter of European patent publication No. 14684.

Herbicidal arylalkylphosphinic acids, such as methyl-(2-methoxyphenyl)phosphinic acid, have been disclosed in U.S. Pat. No. 4,130,410. Bis(phenoxyphenyl)phosphinic acid has been described in J. Med. Chem. 8, 891 (1965), but no mention of herbicidal properties is made.

The compounds of the present invention, namely 2-substituted 5-phenoxyphenylphosphinic acids and derivatives thereof, are, however, novel compounds which have been found to possess excellent selective herbicidal and plant growth regulating properties, as well as fungicidal and, in some cases, bactericidal properties.

The 2-substituted 5-phenoxyphenylphosphinic acid derivatives of the present invention have the formula I

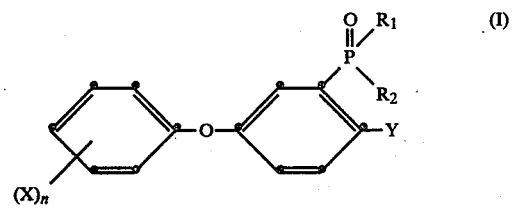

wherein $R_1$ is an unsubstituted or substituted alkyl or aryl radical, $R_2$ is a hydroxyl (OH) group, lower alkoxy, lower alkylthio, alkylamino, dialkylamino or chlorine, X is halogen or a —$CF_3$, —$NO_2$ or —CN group, n is 0 to 3, and Y is —$NO_2$, —$NH_2$, —OH, halogen or —CN.

Alkyl radicals $R_1$ are preferably lower $C_1$–$C_4$ alkyl radicals such as methyl, ethyl, n- and isopropyl and the four possible butyl radicals. These alkyl radicals can also be substituted, especially by halogen such as chlorine, and can be e.g. —$CCl_3$, Cl—$CH_2$— and Cl—$CH_2$—$CH_2$—. Aryl radicals $R_1$ are, in particular, phenyl and substituted phenyl.

Alkoxy, alkylthio, alkylamino and dialkylamino groups $R_2$ contain 1 to 4 carbon atoms in the alkyl moiety. In this case too, the alkyl moiety can be unsubstituted or substituted.

Halogen atoms X and Y are chlorine, bromine or iodine, with chlorine being preferred. The preferred radical Y is the nitro group.

Particularly interesting and preferred herbicidal compounds are those in which n is 2 and both radicals X (as $X_1$ and $X_2$) are in the ortho- and para-position of the phenoxy radical, and each X independently is $NO_2$, CN, $CF_3$ and halogen, especially chlorine.

Especially preferred compounds are 2-substituted 5-(2'-halo-4'-trifluoromethylphenoxy)phenylphosphinic acid derivatives of the formula IV

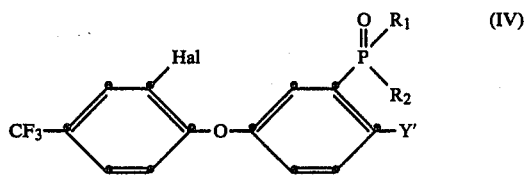

wherein Hal is a halogen atom, in particular a chlorine atom, and Y' is a halogen atom, the cyano group and, in particular, the nitro group.

The novel phosphinic acid derivatives of the formula I are obtained in a manner analogous to the known method of obtaining 2-nitrophenylphosphonic acids (J. Chem. Soc. (C), 1969, 1314), by converting a 1,2-dinitro-5-phenoxybenzene (3,4-dinitrodiphenyl ether) of the formula II

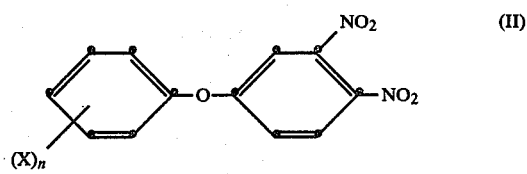

with a O,O-dialkylalkyl- or -arylphosphonite $R_1$—P—(OR')$_2$, wherein R' is lower alkyl and $R_1$ is alkyl or aryl, with the removal of one mole of a compound R'—O—N=O, into an alkyl ester of a 2-nitro-5-phenoxyphenylphosphinic acid of the formula III

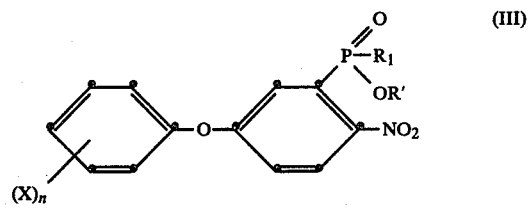

and, if desired, converting said phosphinic acid alkyl ester radical, in a manner known per se, into the corresponding free phosphinic acid or into another derivative thereof, in accordance with the definitions of $R_1$ and $R_2$ in formula I. If desired, the remaining nitro group in 2-position can be replaced by another radical Y.

In the above reaction, which is carried out in the temperature range between 50° and 150° C., preferably between 70° and 120° C., a meta-positioned phosphinic acid ester group results from the nitro group in the meta-position to the phenoxy group, with the removal of one mole of a compound R'—O—N=O, whilst the nitro group in the para-position to the phenoxy group is left unchanged. This is clearly evident from the spectrographic data. The reaction with the phosphonite can be carried out in the absence of a solvent; but it is preferred to conduct the reaction in an organic aprotic solvent such as acetonitrile, benzene or toluene.

The starting materials of the formula II are obtained in accordance with the particulars of European patent publication No. 0007471. The reaction scheme is as follows:

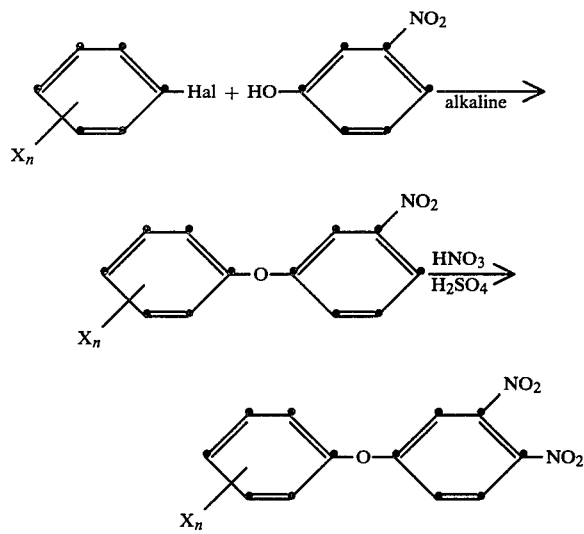

i.e. nitration of a 3-nitrodiphenyl ether which has been obtained from a halobenzene and 3-nitrophenol.

The nitro group (Y=NO₂) which is in the 2-position of the product of the formula III can, if desired, be converted into another group Y. It can be reduced catalytically (using Ni or Pd catalysts) with hydrogen to the amino group (—NH₂).

The amino group can be replaced by halogen or cyano by diazotisation in acid medium with sodium nitrite, and the diazonium salt is reduced or reacted in known manner by the method of Sandmeyer with CuCN or a copper halide (CuI), to yield derivatives in which Y is halogen, the cyano group or the hydroxyl group.

The phosphinate ester group can be readily converted into the phosphinyl chloride (R$_2$=Cl) by treatment with 2 moles of SOCl$_2$, in the presence of dimethyl formamide as catalyst, at elevated temperature (U.S. Pat. No. 4,213,922). By reacting this chloride with primary or secondary alkylamines, alcohols, mercaptans or water, it is possible to replace the chlorine atom by a radical selected from the group consisting of alkylamino, dialkylamino, alkoxy, alkylthio or hydroxyl.

The free phosphinic acids (R$_2$=OH) are also obtained direct from the alkyl esters by treatment with concentrated hydrochloric acid or (CH$_3$)$_3$SiBr and subsequent hydrolysis of the silyl esters with water.

Both the esters and the free acids and their derivatives of the formula I have an excellent herbicidal activity, both in preemergence and postemergence application.

The following Examples illustrate the production of a number of 2-substituted 5-phenoxyphenylphosphinic acid derivatives of the formula I. Further compounds of the formula I obtained in corresponding manner are listed in the subsequent table.

EXAMPLE 1

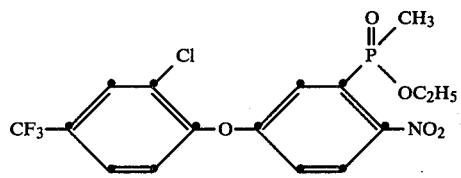

A mixture of 30.9 g (0.085 mole) of 3,4-dinitro-2'-chloro-4'-trifluoromethyl-diphenyl ether and 23.2 g (0.170 mole) of CH$_3$P(OC$_2$H$_5$)$_2$ -diethylmethylphosphonite) in 200 ml of toluene is heated to reflux for 20 hours. The reaction mixture is concentrated in a rotary evaporator and the dark brown resinous residue is chromatographed over silica gel KG 60 (solvent: ethyl acetate/hexane 4:1), affording 22 g of an orange oil. Recrystallisation from diisopropyl ether yields 20.3 g of pale yellow crystals. Further recrystallisation yields 18.6 g (51.6% of theory) of 2-nitro-5-(2'-chloro-4'-trifluoromethylphenoxy)phenylmethylphosphinic acid ethyl ester of the above formula, with a melting point of 106°–107° C.

$^1$H—NMR (in CDCl$_3$) in δ: C—CH$_3$ 1.20 (t,3H),P—CH$_{OCH_3}$ 4.0 (quin, 2H); aromat.H 7–8.2 (m, 6H).

Analysis: C$_{16}$H$_{14}$ClF$_3$NO$_5$P (423.71): Calc.: C 45.36; H 3.33; N 3.31; F 13.45%. Found: C 45.54; H 3.39; N 3.55; F 13.21%.

EXAMPLE 2

A mixture of 7 g of the ester obtained in Example 1, 20 ml of 20% aqueous HCl and 20 ml of ethanol is heated to reflux for 20 hours and then concentrated in a rotary evaporator, affording 6.2 g (98.6% of theory) of the corresponding free phosphinic acid in the form of a glassy substance which is soluble in water.

$^1$H—NMR (in DMSO/CD$_3$OD) in δ: P—CH$_3$ 1.33 (d;J$_{PCH}$ 15 Hz, 3H); aromat.H 6.4–7.7 (m, 6H); OH 4.03 (s, 1H).

EXAMPLE 3

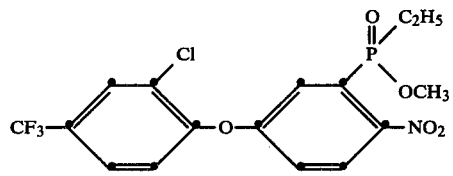

[2-Nitro-5-(2'-chloro-4'-trifluoromethylphenoxy)phenylethylphosphinic acid methyl ester]

A mixture of 36.26 g (100 millimoles) of 3,4-dinitro-2'-chloro-4'-trifluoromethyl-diphenyl ether and 24.42 g (200 millimoles) of O,O-dimethylethylphosphonite

[C₂H₅P(OCH₃)₂] is heated to reflux in 250 ml of toluene under normal pressure for 24 hours. The solvent is then evaporated off under reduced pressure and the residue is distilled under a high vacuum at 180° C. in a bulb tube. The distillate crystallises in the receiver and melts at 61°–63° C. after recrystallisation from diisopropyl ether. Yield: 13.1 g (30.9% of theory).

$^1$H—NMR in CDCl$_3$ in δ: C—CH$_3$ 1.03 (J$_{POCH}$21 Hz, 3H); CH$_2$—C 2.2 (J$_{PCH}$ 15 Hz, 2H); OCH$_3$ 3.55 (J$_{POCH}$ 11 Hz; 3H) aromat.H 7–8.0 (m, 6H) [ppm].

Analysis: C$_{16}$H$_{14}$Cl F$_3$NO$_5$P(423.71): Calc.: C 45.36; H 3.33; N 3.31; F 13.45; Cl 8.37%. Found: C 45 59; H 3.38; N 3.35; F 13.61; Cl 8.14%.

EXAMPLE 4

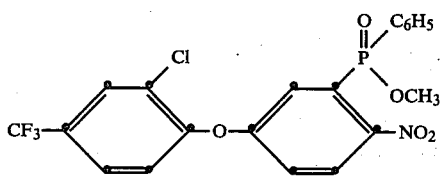

[2-Nitro-5-(2'-chloro-4'-trifluoromethylphenoxy)phenyl-phenylphosphinic acid methyl ester]

A mixture of 36.26 g (100 millimoles) of 3,4-dinitro-2'-chloro-4'-trifluoromethyl-diphenyl ether and 34.03 g (200 millimoles) of O,O-dimethylphenylphosphonite [C$_6$H$_5$P(OCH$_3$)$_2$] is heated to reflux in 250 ml of toluene for 4 hours under a nitrogen atmosphere. The solvent is then evaporated off under reduced pressure and the residue is chromatographed over silica gel 60 with ethyl acetate/hexane (4:1), yielding 25.3 g (53.6%) of pale beige-coloured crystals which melt at 111°–112° C. after recrystallisation from diisopropyl ether.

Analysis: C$_{20}$H$_{14}$ClF$_3$NO$_5$P (471.76): Calc.: C 50.92; H 2.99; N 2.97; F 12.08; Cl 7.51%. Found: C 50.83; H 3.02; N 3.02; F 12.28; Cl 7.54%.

$^1$H—NMR in CDCl$_3$ in δ: OCH$_3$ 3.65 (d, J$_{POCH}$ 11 Hz, 3H) P—C$_6$H$_5$ and aromat.H 7–8.0 (m, 11H) [ppm].

EXAMPLE 5

2-Nitro-5-(2'-chloro-4'-trifluoromethylphenoxy)-phenylmethylphosphinic acid methyl ester A mixture of 60.0 g of 3,4-dinitro-2'-chloro-4'-trifluoromethyldiphenyl ether and 35.8 g of O,O-dimethylmethylphosphonite [CH$_3$—P(OCH$_3$)$_2$] is heated to reflux in 400 ml of toluene for 16 hours, with stirring. During this time CH$_3$—O—NO escapes as gas. The reaction mixture is then concentrated in a rotary evaporator and the residue is crystallised by adding diisopropyl ether and stirring. The crystals are dissolved in ethyl acetate and the solution is filtered over 300 g of silica gel 60 and concentrated. Recrystallisation from diisopropyl ether yields 34.0 g (50.1% of theory) of pale yellow crystals with a melting point of 123°–124° C.

$^{31}$P-chemical displacement (in CDCl$_3$)-40,0 ppm.

$^1$H (in CDCl$_3$) in δ: CH$_3$—P 2,03 ppm (d, J$_{PCH}$ 16 Hz, 3H); OCH$_3$ 3,8 ppm (d,J$_{POCH}$ 11,6 Hz, 3H); aromat.H 7,9–8,3 ppm (m,6H).

Analysis: C$_{15}$H$_{12}$ClF$_3$NO$_5$P (409,7): Calc.: C 43.98; H 2.95; N 3.42; Cl 8.65; F 13.91; P 7.56%. Found: C 43.93; H 2.99; N 3.39; Cl 8.83; F 14.18; P 7.63%.

EXAMPLE 6

2-Nitro-5-(2'-chloro-4'-trifluoromethylphenoxy)-phenylmethylphosphinic acid n-butyl ester 36.3 g (0.1 mole) of 3,4-dinitro-2'-chloro-4'-trifluoromethyldiphenyl ether are dissolved in 200 ml of toluene and the solution is heated to reflux. Then 21.15 g (0.11 mole) of O,O-di-n-butylmethylphosphonite are added dropwise to the boiling solution over ½ hour and the mixture is refluxed for a further 16 hours, with stirring. After chromatography over a column of silica gel with ethyl acetate (100%), concentration of the second fraction (2 liters) gives an orange oil which crystallises from diisopropyl ether. Yield: 10.8 g (24% of theory) of beige-coloured crystals with a melting point of 45°–46° C.

$^1$H—NMR (in CDCl$_3$) in δ: P—CH$_3$+C$_3$H$_7$ 0,8–2,2 (m, 10H); OCH$_2$ 3,9 (m, 2H); aromat.H 7–8,2 (m, 6H) [ppm].

Analysis: C$_{18}$H$_{18}$ClF$_3$NO$_5$P (451,8): Calc.: C 47.85; H 4.02; N 3.1; Cl 7.85; F 12.61; P 6.86%. Found: C 48.3; H 4.3; N 3.0; Cl 7.6; F 12.2; P 6.7%.

The above compounds and further compounds of the formula

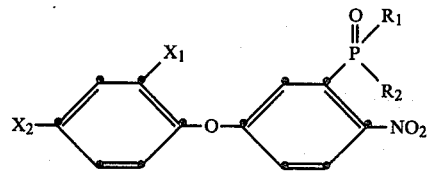

obtained in analogous manner are listed in the following table:

| Compound | X$_1$ | X$_2$ | R$_1$ | R$_2$ | Physical data |
|---|---|---|---|---|---|
| 1 | Cl | CF$_3$ | CH$_3$ | —OC$_2$H$_5$ | m.p. 106–107° C. |
| 2 | Cl | CF$_3$ | CH$_3$ | —OH | glassy, water-soluble |
| 3 | Cl | CF$_3$ | C$_2$H$_5$ | —OCH$_3$ | m.p. 61–63° C. |
| 4 | Cl | CF$_3$ | Phenyl | —OCH$_3$ | m.p. 111–112° C. |
| 5 | Cl | CF$_3$ | CH$_3$ | —OCH$_3$ | m.p. 123–124° C. |
| 6 | Cl | CF$_3$ | CH$_3$ | —O—C$_4$H$_9$(n) | m.p. 45–46° C. |
| 7 | NO$_2$ | CF$_3$ | CH$_3$ | —OC$_2$H$_5$ | |
| 8 | NO$_2$ | Cl | C$_2$H$_5$ | —OCH$_3$ | |
| 9 | NO$_2$ | CF$_3$ | CH$_3$ | OH | |
| 10 | CN | CF$_3$ | CH$_3$ | —OC$_2$H$_5$ | |
| 11 | CF$_3$ | NO$_2$ | Phenyl | —OC$_3$H$_7$(n) | |
| 12 | NO$_2$ | Cl | —CCl$_3$ | —OCH$_3$ | |
| 13 | Cl | CF$_3$ | (—CH$_2$)$_2$—Cl | —OC$_2$H$_5$ | |
| 14 | CF$_3$ | CN | —CH$_2$Cl | —OC$_4$H$_9$ | |
| 15 | CF$_3$ | NO$_2$ | Phenyl | —OH | |
| 16 | Cl | CF$_3$ | C$_2$H$_5$ | —OC$_3$H$_7$(iso) | |
| 17 | Cl | CF$_3$ | C$_2$H$_5$ | —OC$_4$H$_9$(tert.) | |

Further selected compounds of the formula

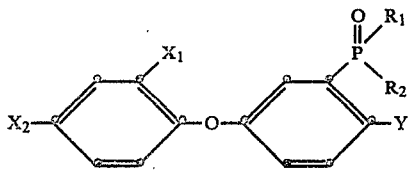

are listed in the following table:

| Compound | X₁ | X₂ | R₁ | R₂ | Y |
|---|---|---|---|---|---|
| 18 | Cl | CF₃ | CH₃ | —OC₂H₅ | NH₂ |
| 19 | Cl | CF₃ | C₂H₅ | —OCH₃ | NH₂ |
| 20 | Cl | CF₃ | CH₃ | —OCH₃ | OH |
| 21 | Cl | CF₃ | C₂H₅ | —OCH₃ | OH |
| 22 | Cl | CF₃ | CH₃ | —OC₂H₅ | Cl |
| 23 | Cl | CF₃ | C₂H₅ | —OCH₃ | Cl |
| 24 | Cl | CF₃ | CH₃ | —OC₄H₉(n) | Br |
| 25 | Cl | CF₃ | CH₃ | —OCH₃ | Br |
| 26 | Cl | CF₃ | CH₃ | —OC₃H₇ | I |
| 27 | Cl | CF₃ | phenyl | —OCH₃ | CN |
| 28 | Cl | CF₃ | CH₃ | —OC₂H₅ | CN |
| 29 | Cl | CF₃ | CH₃ | Cl | NO₂ |
| 30 | Cl | CF₃ | n-C₃H₇ | —OCH₃ | NO₂ |
| 31 | Cl | CF₃ | t-C₄H₉ | —OCH₃ | NO₂ |

The novel phosphinic acid derivatives of the formula I are compounds which are stable at temperatures below 160° C. and soluble in conventional organic solvents.

For use as herbicides or plant growth regulators, the novel compounds can be employed by themselves or, preferably, together with suitable carriers and/or other adjuvants, in the form of compositions.

The preferred utility of the compounds of the formula I is as preemergence and postemergence herbicides, whilst many of the compounds are translocated in the plant and some have good selective properties. As plant growth regulators the compounds of the formula I, when applied in low concentrations, in particular inhibit the growth of monocot and dicot plants and also desiccate parts of plants above the ground.

Those compounds of the formula I which have low selectivity are most suitable for use as postemergence knock-down agents for the rapid and total destruction and desiccation of plant cover and plant populations which are undesirable or are to be replaced.

Such a field of use is e.g. the destruction of convolvulus species in vineyards, where e.g. compound 1 of the table is very effective in a concentration of 2 kg/ha.

A still more important field of use opened up by the rapid and total contact action of a number of the novel compounds, e.g. compounds 1 and 3, is the total regeneration of a harvested crop area or of a pasture by the rapid destruction (desiccation) of the entire flora and the resowing of another crop without ploughing up the soil beforehand.

In this no tillage system the soil is no longer ploughed before sowing the new crop. The weed cover or the remaining plants of a previously harvested cereals crop (stubble) are totally destroyed in a few days (to at most 2 weeks) by rapidly acting herbicides instead of by the plough. A new crop is then sown, in rows, in the perished plant cover by means of special sowing machines.

This method suggests itself in areas which are endangered by erosion through wind and water, and also where it is intended to save on machines, energy and labour, and especially in areas where, after the harvesting of a first crop, the subsequent crop must be quickly gathered in, as in a crop rotation:

wheat ⟶ soybean or maize or cotton grass ⟶ soybean or maize or cotton
(pasture or artificial grassland)

soybean stubble ⟶ maize maize stubble ⟶ soybean

Usually, there is used not only one herbicide alone, but a mixture of 3 herbicides. One of the components is always a rapid acting herbicide; as such, Paraquat has primarily up to now been used, mixed with e.g. Atrazine or an acetanilide.

Some of the compounds of the present invention, e.g. compounds 1 and 3, have properties which enable them to assume completely the role of Paraquat (1,1-dimethyl-4,4-bipyridylium dichloride) in the no tillage system mentioned above, without having the disadvantages of this compound (mammalian toxicity) to the same extent.

The compositions of the present invention are obtained in known manner by intimately mixing and grinding active ingredients (compounds) of the general formula I with suitable carriers and/or adjuvants, if desired with the addition of antifoams, wetting agents, dispersants and/or solvents which are inert to the active ingredients. The active ingredients can be processed to the following formulations:

solid formulations: dusts, tracking powders, granules (coated granules, impregnated granules and homogeneous granules);

active ingredient concentrates which are dispersible in water: wettable powders, pastes, emulsions, emulsifiable concentrates;

liquid formulations: solutions.

The concentrations of active ingredient in the commercial compositions of this invention are between 1 and 80 percent by weight and can be diluted, before use, to lower concentrations of about 0.05 to 1 percent by weight.

The compositions of the present invention can be mixed with other biocidal compounds. For example, in addition to containing the compounds of the general formula I, the compositions can also contain e.g. insecticides, fungicides, bactericides, fungistats, bacteriostats, nematocides or further herbicides, in order to broaden the activity spectrum.

The following Examples will serve to illustrate in more detail the preparation of solid and liquid formulations containing the compounds of the invention. Throughout, parts and percentages are by weight.

Granules

The following substances are used to formulate 5% granules:
5 parts of compound 1 [2-nitro-5-(2'-chloro-4'-trifluoromethylphenoxy)phenylmethylphosphinic acid ethyl ester],
0.25 part of epoxidised vegetable oil,
0.25 part of cetyl polyglycol ether,
3.50 parts of polyethylene glycol,
91 parts of kaolin (particle size 0.3–0.8 mm).

The active ingredient is mixed with the epoxidised vegetable oil and the mixture is dissolved in 6 parts of acetone; then polyethylene glycol and cetyl polyglycol ether are added. The resultant solution is sprayed on kaolin and subsequently evaporated in vacuo.

Wettable Powders

The following constituents are used to formulate (a) a 70% and (b) a 10% wettable powder:

(a)

70 parts of 2-nitro-5-(2'-chloro-4'-trifluoromethylphenoxy)phenylethylphosphinic acid ethyl ester (compound 3),
5 parts of sodium dibutylnaphthylsulfonate,
3 parts of naphthalenesulfonic acid/phenolsulfonic acid/formaldehyde condensate (3:2:1),
10 parts of kaolin,
12 parts of Champagne chalk;

(b)

10 parts of 2-nitro-5-(2'-chloro-4'-trifluoromethylphenoxy)phenylmethylphosphinic acid (compound 2),
3 parts of a mixture of the sodium salts of saturated fatty alcohol sulfates,
5 parts of naphthalenesulfonic acid/formaldehyde condensate,
82 parts of kaolin.

The active ingredient is applied to the corresponding carriers (kaolin and chalk) and then these are mixed and ground, affording wettable powders of excellent wettability and suspension power. By diluting these wettable powders with water it is possible to obtain suspensions containing 0.1 to 80% of active ingredient. These suspensions are suitable for controlling weeds in cultivations of plants.

Paste

The following substances are used to formulate a 45% paste:

45 parts of 2-nitro-5-(2'-chloro-4'-trifluoromethylphenoxy)phenylphenylphosphinic acid methyl ester (compound 4) or another compound of the formula I,
5 parts of sodium aluminium silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active ingredient is intimately mixed with the adjuvants in appropriate devices and ground. By diluting the resultant paste with water, it is possible to prepare suspensions of the desired concentration.

Emulsifiable Concentrate

The following ingredients are mixed to formulate a 25% emulsifiable concentrate:

25 parts of 2-nitro-5-(2'-chloro-4'-trifluoromethylphenoxy)phenylmethylphosphinic acid n-butyl ester (compound 6),
5 parts of a mixture of nonylphenolpolyoxyethylene and calcium dodecylbenzenesulfonate,
15 parts of cyclohexanone,
55 parts of xylene.

This concentrate can be diluted with water to give emulsions of suitable concentrations of e.g. 0.1 to 10%. Such emulsions are suitable for controlling weeds in crops of cultivated plants.

The following test methods are employed to establish the utility of the compounds of the formula I as preemergence and postemergence herbicides.

Preemergence Herbicidal Action (Inhibition of Germination)

In a greenhouse, immediately after sowing the test plants in seed dishes, the surface of the soil is treated with an aqueous dispersion of the active ingredients, obtained from a 25% emulsifiable concentrate or from a 25% wettable powder with compounds which, on account of their insufficient solubility, cannot be formulated to an emulsifiable concentrate. A concentration is used which corresponds to 4 kg of active ingredient per hectare. The seed dishes are kept in the greenhouse at 22°–25° C. and 50–70% relative humidity. The test is evaluated 3 weeks later according to the following rating:

1 = plants have not germinated or are totally withered
2–3 = very strong action
4–6 = average action
7–8 = slight action
9 = no action (as untreated control)
— = plant not tested in corresponding active ingredient concentration.

Postemergence Herbicidal Action (Contact Herbicide)

A large number (at least 7) of weeds and cultivated plants, both monocots and dicots, are sprayed postemergence, in the 4- to 6-leaf stage, with an aqueous dispersion in a concentration of 4 kg of active ingredient per hectare and kept at 24°–26° C. and 45–60% relative humidity. The test is evaluated at least 15 days after treatment, using the same rating as employed in the preemergence test.

The results obtained in these tests with the compounds of Examples 1, 2, 3, 5 and 6, as well as with the compounds known from German Offenlegungsschrift No. 2 619 841, viz. 2-nitro-5-chlorophenylphosphonic acid diethyl ester (A) and 2-nitrophenylphosphonic acid diethyl ester (B), are reported in the following table:

| Compound | 1 | 2 | 3 | 5 | 6 | A | B |
|---|---|---|---|---|---|---|---|
| Preemergence test 4 kg per hectare Plant | | | | | | | |
| avena fatua | 2 | 9 | 2 | 1 | 6 | 9 | 9 |
| sinapis alba | 1 | 1 | 1 | 1 | 1 | 9 | 9 |
| setaria italica | 2 | 2 | 1 | 1 | 3 | 9 | 9 |
| stellaria media | 1 | 7 | 1 | 1 | 1 | 9 | 9 |
| Postemergence test 4 kg per hectare Plant | | | | | | | |
| avena fatua | 4 | 4 | 1 | 2 | 5 | 8 | 4 |
| setaria italica | 2 | 1 | 1 | 3 | 4 | 6 | 4 |
| lolium perenne | 5 | 4 | 1 | 3 | 4 | 7 | 4 |
| solanum nigrum | 1 | 1 | 1 | 1 | 1 | 6 | 5 |
| sinapis alba | 1 | 1 | 1 | 1 | 1 | 5 | 5 |
| stellaria media | 2 | 2 | 1 | 2 | 2 | 6 | 7 |

Both in the preemergence and in the postemergence test the compounds of the invention are very effective against monocot and dicot weeds. Of the simultaneously tested comparison compounds, unsatisfactory ratings of 5 to 9 are obtained with 2-nitrophenylphosphonic acid diethyl ester, whilst 2-nitro-5-chlorophenylphosphonic acid diethyl ester exhibits weak herbicidal action only in the postemergence test.

What is claimed is:

1. A phosphinic acid derivative of the formula

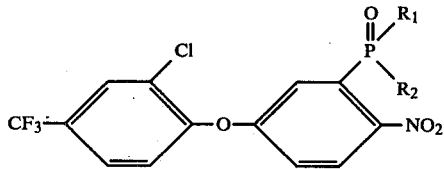

in which
R$_1$ is C$_1$–C$_4$ alkyl optionally substituted by chlorine, or is phenyl, and
R$_2$ is hydroxy, C$_1$–C$_4$ alkoxy or chlorine.

2. A phosphinic acid derivative according to claim 1 wherein R$_1$ is methyl, ethyl or phenyl and R$_2$ is C$_1$–C$_4$alkoxy.

3. A phosphinic acid derivative according to claim 2 which is 2-nitro-5-(2'-chloro-4'-trifluoromethylphenoxy)phenylmethylphosphinic acid ethyl ester.

4. A phosphinic acid derivative according to claim 2 which is 2-nitro-5-(2'-chloro-4'-trifluoromethylphenoxy)phenylethylphosphinic acid methyl ester.

* * * * *